(12) United States Patent
Flörke et al.

(10) Patent No.: US 11,780,627 B2
(45) Date of Patent: Oct. 10, 2023

(54) METHOD AND FILLING MACHINE FOR FILLING PACKAGES THAT ARE OPEN ON ONE SIDE

(71) Applicant: SIG Technology AG, Neuhausen am Rheinfall (CH)

(72) Inventors: Rudolf Flörke, Juelich (DE); Hans-Willi Mainz, Heinsberg (DE)

(73) Assignee: SIG Technology AG, Neuhausen am Rheinfall (CH)

( * ) Notice: Subject to any disclaimer, the term of this patent is extended or adjusted under 35 U.S.C. 154(b) by 839 days.

(21) Appl. No.: 16/488,761

(22) PCT Filed: Feb. 2, 2018

(86) PCT No.: PCT/EP2018/052613
§ 371 (c)(1),
(2) Date: Aug. 26, 2019

(87) PCT Pub. No.: WO2018/158032
PCT Pub. Date: Sep. 7, 2018

(65) Prior Publication Data
US 2021/0139179 A1    May 13, 2021

(30) Foreign Application Priority Data
Feb. 28, 2017   (DE) .................. 10 2017 104 153.2

(51) Int. Cl.
*B65B 55/04*    (2006.01)
*B65B 43/54*    (2006.01)
(Continued)

(52) U.S. Cl.
CPC .............. *B65B 55/04* (2013.01); *A61L 2/07* (2013.01); *A61L 2/208* (2013.01); *A61L 2/26* (2013.01);
(Continued)

(58) Field of Classification Search
None
See application file for complete search history.

(56) References Cited

U.S. PATENT DOCUMENTS 5,879,648 A * 3/1999 Hada .................... A61L 2/20
                                                    422/305
7,806,680 B2 * 10/2010 Adriansens ............ B65B 3/022
                                                    425/526
(Continued)

FOREIGN PATENT DOCUMENTS

CN    101203428 A    6/2008
CN    102470945 A    5/2012
(Continued)

*Primary Examiner* — Tanzim Imam
(74) *Attorney, Agent, or Firm* — The Webb Law Firm (57) ABSTRACT

Described and depicted is a method for filling packages that are open on one side, in particular cardboard composite packages, with free-flowing products, in particular foodstuffs, in a filling machine. In order to allow the heating, sterilisation and/or drying to be carried out at high throughputs more reliably and with less complexity in terms of the equipment and/or method, it is provided that preheating air and/or drying air and/or sterilising agent is introduced into the packages that are open on one side and that a volume of preheating air and/or drying air and/or sterilising agent, said volume corresponding to at least three times the volume of the package that is open on one side, is introduced into at least one, preferably at least substantially each, package that is open on one side.

16 Claims, 4 Drawing Sheets

(51) Int. Cl.
  *B65B 43/10* (2006.01)
  *B65B 3/02* (2006.01)
  *A61L 2/20* (2006.01)
  *A61L 2/07* (2006.01)
  *A61L 2/26* (2006.01)

(52) U.S. Cl.
  CPC .............. *B65B 3/025* (2013.01); *B65B 43/10* (2013.01); *B65B 43/54* (2013.01); *A61L 2202/15* (2013.01); *A61L 2202/23* (2013.01)

(56) References Cited

U.S. PATENT DOCUMENTS

| | | | |
|---|---|---|---|
| 2002/0029543 A1 | 3/2002 | Taggart | |
| 2004/0208781 A1 | 10/2004 | Hayashi et al. | |
| 2007/0271873 A1* | 11/2007 | Baltes | B65B 51/225 53/266.1 |
| 2008/0190072 A1* | 8/2008 | Lindblad | B65B 55/10 53/426 |
| 2009/0081326 A1 | 3/2009 | Adriansens et al. | |
| 2010/0047120 A1 | 2/2010 | Adrianseue et al. | |
| 2010/0276029 A1* | 11/2010 | Sangi | B67C 7/0073 141/1 |
| 2014/0178250 A1* | 6/2014 | Loy | B29C 49/4252 422/292 |
| 2016/0376045 A1* | 12/2016 | Seiche | B65B 3/025 53/426 |
| 2017/0001744 A1* | 1/2017 | Konze | B65B 55/02 |

FOREIGN PATENT DOCUMENTS

| | | | |
|---|---|---|---|
| DE | 3036972 A1 | 4/1982 | |
| DE | 3339930 A1 | 5/1985 | |
| DE | 19546353 A1 | 6/1996 | |
| DE | 19945500 A1 | 4/2000 | |
| DE | 19949692 A1 | 4/2001 | |
| DE | 102014000701 A1 * | 7/2015 | ............... B65B 1/06 |
| EP | 0597356 A2 | 5/1994 | |
| EP | 2746029 A1 | 6/2014 | |
| GB | 2084467 B | 10/1984 | |
| JP | S6437329 A | 2/1989 | |
| JP | H02242721 A | 9/1990 | |
| JP | H09240629 A | 9/1997 | |
| JP | H10119934 A | 5/1998 | |
| JP | 2003325645 A | 11/2003 | |
| JP | 2009018851 A | 1/2009 | |
| JP | 2010100295 A | 5/2010 | |
| JP | 2012082013 A | 4/2012 | |
| JP | 2014204814 A | 10/2014 | |
| WO | 03022689 A1 | 3/2003 | |
| WO | 2011002381 A1 | 1/2011 | |

* cited by examiner

METHOD AND FILLING MACHINE FOR FILLING PACKAGES THAT ARE OPEN ON ONE SIDE

CROSS-REFERENCE TO RELATED APPLICATIONS

This application is the United States national phase of International Application No. PCT/EP2018/052613 filed Feb. 2, 2018, and claims priority to German Patent Application No. 10 2017 104 153.2 filed Feb. 28, 2017, the disclosures of which are hereby incorporated by reference in their entirety.

BACKGROUND OF THE INVENTION

Field of the Invention

The invention relates to a method for filling packages that are open on one side, in particular cardboard composite packages, with free-flowing products, in particular foodstuffs, in a filling machine in which preheating air, drying air and/or sterilising agent is introduced into the packages that are open on one side. The invention further relates to a filling machine for filling packages that are open on one side, in particular cardboard composite packages, with free-flowing products, in particular foodstuffs, wherein at least one nozzle is provided for introducing preheating air, drying air and/or sterilising agent from above into the packages that are open on one side, and wherein a transport device is provided for transporting the packages that are open on one side through the filling device.

Description of Related Art

Various filling machines for filling packages that are open on one side with products, in particular in the form of foodstuffs, are already known. The packages are preferably filled with free-flowing foodstuffs by corresponding filling machines. The packages used are, in particular, packages that are open at an upper side in order to provide an opening for filling the packages. The packages can, for example, be cardboard composite packages that consist of a package material in the form of a laminate comprising a cardboard layer and outer, in particular thermoplastic, plastic layers, for instance made of polyethylene (PE). The cardboard confers sufficient stability on the packages, so that the packages can be easily handled and for example stacked. The plastic layers protect the cardboard from moisture and enable the package material to be sealed to form a tight package. In addition, further layers, such as an aluminium layer, can be provided that prevent oxygen and other gases from diffusing through the package.

The packages are typically filled with food under sterile conditions. In this case, not only the foodstuff to be filled, but also the package, is to be sterilised. For this purpose, the foodstuffs are normally heated for a certain period of time. First the packages are usually flushed with sterile preheating air. A sterilising agent that typically is or at least comprises hydrogen peroxide is then introduced into the packages heated in this way. Since the package is preheated, high reaction speeds are achieved during the sterilisation, and excessive condensate is prevented from forming in the package. Moisture and residual hydrogen peroxide are subsequently removed from the package by drying the package with, preferably hot and sterile, drying air. The sterile package is then filled.

During the sterilisation and/or filling, the packages can be transported continuously, as necessary at a constant speed, through the filling machine. The device for introducing preheating air, sterilising agent, drying air and/or product to be filled comprises nozzles for targeted delivery of the corresponding medium, which can be moved with the packages, so that there is substantially no relative speed between the nozzles and the packages during the introduction of preheating air, sterilising agent, drying air and/or product to be filled. However, it is frequently the case that the packages are moved cyclically, that is to say stepwise, through the filling machine such that, for a certain period of time, the packages successively assume certain positions in which the packages can be subjected, in a stationary manner via at least one nozzle, to preheating air, sterilising agent, drying air and/or product to be filled.

If too little time remains in one cycle to introduce a sufficient quantity of preheating air, sterilising agent, drying air and/or product to be filled into the package in a suitable manner, the introduction of preheating air, sterilising agent, drying air and/or product to be filled can also be carried out successively, stepwise, via different nozzles in a plurality of consecutive processing positions in which the packages come to a standstill for a short time. On the other hand, in the case of packages that are moved continuously through the filling machine, the period of time for the introduction of preheating air, sterilising agent, drying air and/or product to be filled, for example, is extended. As a result, however, the filling machine is also extended and the cyclical transport of at least the nozzles of the devices for introducing preheating air, sterilising agent, drying air and/or product to be filled is made difficult in the filling machine. In order to compensate for this, the processing times for heating, sterilising, drying and/or filling the packages are reduced, which may result in problems with the reliability of the corresponding processing.

The disadvantage of the known methods is consequently the complexity required, in terms of equipment and method, for the heating, sterilisation and/or drying, which can be considerable in particular in the case of high throughputs. Alternatively or additionally, in known methods there is the problem that the heating, sterilisation and/or drying takes place in an unreliable manner, which leads to lower product quality or a higher rate of rejects.

The object underlying the present invention is therefore to design and further develop the method and the filling machine of the type explained in greater detail above such that the heating, sterilisation and/or drying can be carried out at high throughputs more reliably and with less complexity in terms of equipment and/or method.

SUMMARY OF THE INVENTION

This object is achieved by a method for filling packages that are open on one side, in particular cardboard composite packages, with free-flowing products, in particular foodstuffs, in a filling machine,
  in which preheating air, drying air and/or sterilising agent
    is introduced into the packages that are open on one side and
  in which a volume of preheating air and/or drying air and/or sterilising agent, said volume corresponding to at least three times the volume of the package that is open on one side, is introduced into at least one, preferably at least substantially each, package that is open on one side.

The object mentioned is moreover achieved in a filling machine in that adjustment means and introduction means are provided for introducing a volume of preheating air and/or drying air and/or sterilising agent, said volume corresponding to at least three times the volume of the package that is open on one side, into at least one, preferably at least substantially each, package that is open on one side.

It is thus possible to introduce only one of said media, namely the preheating air, the drying air or the sterilising agent with at least three times the volume of the at least one package that is open on one side, into the at least one package that is open on one side. It is also possible, however, for two or all three of the said media to be introduced separately with three times the volume of the at least one package that is open on one side, into the at least one package that is open on one side.

By flushing out the packages with a surplus media volume of preheating air, drying air and/or sterilising agent, more expedient processing of the packages in terms of heating, sterilisation and/or drying is achieved. Thus, it is not only reliably ensured that the heating, sterilisation and/or drying takes place in the desired manner, but the corresponding processing of the packages can also be carried out in a rapid manner with low complexity in terms of equipment. The corresponding surplus of medium in the form of pre-heating air, sterilising agent and/or drying air therefore tends to consume more medium, but as a result the processing can be achieved more rapidly, more reliably and more easily. For example, the use of a corresponding surplus of preheating air, drying air and/or sterilising agent can allow one processing station to be dispensed with because the processing can be ensured in fewer processing stations such that overall, time and complexity in terms of equipment can be reduced.

The packages to be processed can generally have common sizes and thus common volumes. Particularly preferred for fluidic reasons are packages with a volume of at least 100 ml, at least 200 ml or at least 250 ml. In the case of very large packages, a very large quantity of preheating air, sterilising agent and/or drying air is also required, which is why the package size should not exceed 2000 ml, in particular 1500 ml, more particularly 1000 ml.

The described advantages can generally be obtained either during heating, sterilising and/or drying. However, since different boundary conditions are to be taken into account for each of these individual method steps, it is not necessary to use a surplus of preheating air, drying air and sterilising agent, and in any case not with the same surplus. The adaptation of the individual method steps and a possible surplus of medium for the individual method steps may vary. This naturally also applies to the possible surpluses of media for the individual method steps of heating, drying and/or sterilising the packages.

According to the invention, it can thus be sufficient, for example, if the preheating air, the drying air or the sterilising agent is introduced into the at least one package that is open on one side in a quantity that corresponds to at least three times the volume of the package that is open on one side. One or two of said media can, on the other hand, be introduced into the at least one package that is open on one side in a volume smaller than three times the volume of the package that is open on one side. If this leads to preferred results, the preheating air, the drying air and the sterilising agent can also be introduced into the at least one package that is open on one side in different volumes, although the volumes can in each case correspond to at least three times the volume of the package that is open on one side. Alternatively, at least two of said media with an at least substantially identical volume can also be introduced into the at least one package.

Below, a detailed distinction is therefore not always made between the heating, drying and/or sterilisation, and between pre-heating air, drying air and/or sterilising agent. Given the context however, it will be clear to the person skilled in the art which feature is preferred in each case with regard to the preheating, drying and/or sterilisation.

Generally, it is also possible to use a smaller surplus of preheating air, drying air and/or sterilising agent. However, the advantage discussed in the present case results, to a particular extent only with a volume of medium at least substantially three times the volume of the individual packages to be processed. In other words, the effect achieved by a volume of medium at least three times the package volume is several times greater than when a volume of medium is used that is only slightly greater than the volume of the individual packages to be processed.

For the sake of simplicity, the volume of the package that is open on one side can be understood to mean the volume of the package after closing, in particular the filling volume of the package. Preferably, however, this means the entire volume provided in the open state by the package that is open on one side. Depending on the package, the volume of the package when open on one side can be significantly greater than the volume of the closed package or the filling volume thereof.

In the present case, the terms "preheating air" and "drying air" should preferably be interpreted very broadly. Generally, this is hot air as necessary. The corresponding medium is used for heating or drying, which could also be achieved without any air, but with another gas. Thus, if "preheating air" and/or "drying air" are referred to, the term "air" is preferably to be generally regarded as a gas or mixture of gases. However, since air is suitable and available at low cost, it is particularly preferred, if it is really air. Air is also consistently used in practice. Therefore, in the present case, for the sake of greater clarity and to avoid unnecessary repetition, reference is made to "preheating air" and "drying air", even if it is not necessary to restrict these media and said media could in principle also be referred to as to as "heating medium" or "drying medium". The preheating air and/or the drying air can, for example, have a temperature of up to 340° C. In many cases, however, it may be sufficient if the temperature is up to 260° C. or lower. The higher the temperature, the more rapidly the package can be heated or dried. In particular, hydrogen peroxide is suitable as a sterilising agent. Hydrogen peroxide can be introduced together with steam and/or air into the packages that are open on one side. The temperature of the sterilising agent can, for example, be up to 340° C. or, as necessary, up to 290° C. or below.

The packages are preferably laminated packages that are formed from package material laminates. In a particularly preferred case, they are cardboard composite packages made of a package material laminate comprising at least one cardboard layer, preferably at least one barrier layer, for instance consisting of aluminium, polyamide and/or an ethylene-vinyl alcohol, and outer layers made of a thermoplastic material, in particular polyethylene (PE). The longitudinal edges of a packaging material blank formed from the packaging material laminate are sealed together to form a so-called package sleeve. One of the open ends of the package sleeve can be folded together and sealed to form a package base. After filling, the end of the package sleeve that is still open can likewise be closed by folding and sealing to form a package head.

The adjustment means and introduction means for introducing a volume of preheating air, drying air and/or sterilising agent into the packages that are open on one side can be designed to be very different depending on the application. In particular, use can be made of means known from the prior art for adjusting and introducing corresponding media in other applications. A regulating device and/or a control device can be used for adjusting the volume of preheating air, drying air and/or sterilising agent, depending on whether the volume is to be regulated or controlled. Valves and/or pumps coupled to the regulating device and/or control device can be provided for introduction.

In order to save preheating air, drying air and/or sterilising agent, it is possible for the preheating air, the drying air and/or the sterilising agent to be guided only cyclically into the packages that are open on one side, when said packages are positioned under the corresponding outlets. On the other hand, while the packages are transported further, the discharge of preheating air, drying air and/or sterilising agent can be interrupted. However, it is possible and simpler in terms of equipment and control technology if preheating air, drying air and/or sterilising agent continuously flows out of the introduction means or the corresponding outlets.

Independently of a cyclical or continuous outflow of preheating air, drying air and/or sterilising agent, it is possible for the preheating air, the drying air or the sterilising agent to be guided, in only one position or in different positions, that is to say in a plurality of consecutive steps, into the packages that are open on one side. If preheating air, drying air and/or sterilising agent is introduced in a plurality of consecutive steps into the at least one package that is open on one side, it is possible, as necessary in at least one or as necessary in each of the individual steps, to introduce a volume of preheating air, drying air and/or sterilising agent, said volume exceeding or being less than at least three times the volume of the package that is open on one side, into the at least one package that is open on one side. However, it can be provided that the preheating air as a whole, the drying air as a whole and/or the sterilising agent as a whole, is introduced together, as necessary in a plurality of consecutive steps, in a quantity that corresponds to at least three times the volume of the package that is open on one side, into the at least one package that is open on one side.

In order to detect the respective volume of preheating air introduced, drying air introduced and/or sterilising agent introduced into a package, it is furthermore possible, regardless of the above-described manner in which the pre-heating air, the drying air and/or the sterilising agent is introduced into the package that is open on one side, to use at least one sensor, for example a flow sensor. Corresponding flow sensors preferably detect the volume and/or the mass of the medium conveyed, the volume and the mass correlating in a known manner. Provided that preheating air, drying air and/or sterilising agent continuously exit the introduction means of the filling machine, the introduced volume of preheating air, drying air and/or sterilising agent can be determined on the basis of the respective volumetric flow rate, the residence time under the respective introduction means and the type of cyclical or continuous transport of the packages that are open on one side.

According to the invention, it may be sufficient if a volume of preheating air, drying air and/or sterilising agent, said volume corresponding to at least three times the volume of the package that is open on one side, is introduced into package that is open on one side. It is self-evident, however, that the advantage according to the invention is only felt to a greater extent when a volume of preheating air, drying air and/or sterilising agent that corresponds to at least three times the volume of the package that is open on one side is introduced into at least a plurality of packages that are open on one side, in particular at least substantially all of the packages that are open on one side. It is generally preferable for all the packages that are open on one side to be treated in the same manner in the filling machine, since this is simpler in terms of equipment and control technology. Nevertheless, it may be irrelevant for the advantage to be achieved according to the invention if a package that is open on one side or individual packages that are open on one side is or are treated in a manner that is different and, as necessary, not in accordance with the invention.

For the sake of greater clarity and to avoid unnecessary repetition, the method and the filling machine for filling packages that are open on one side are described jointly below, without a detailed distinction being made between the method and the filling machine.

However, given the context it is clear to the person skilled in the art which feature is preferred in each case with regard to the method and the Ailing machine. In addition, the invention may only relate to the introduction of the preheating air, of the drying air or of the sterilising agent alone. As necessary, however, it may be preferred if the invention relates to the introduction of at least two of said media, namely the preheating air, the drying air and the sterilising agent. Alternatively, however, it can be preferred if the invention relates separately to the introduction of the preheating air, the introduction of the drying air and the introduction of the sterilising agent respectively. For the sake of greater clarity and to avoid unnecessary repetition, the invention is therefore described jointly for the different media, taking account of the above. However, all media do not necessarily have to be meant jointly at all times.

In a first particularly preferred method, a volume of preheating air, drying air and/or sterilising agent said volume corresponding to at least four times the volume of the package that is open on one side, is introduced into the at least one, preferably at least substantially each, package that is open on one side. In this way, reliable preheating, drying and/or sterilisation is achieved with a low level of equipment and/or time expenditure.

This is the case in particular when a volume of preheating air, drying air and/or sterilising agent said volume corresponding to at least six times, in particular at least ten times the volume of the package that is open on one side, is introduced into at least one, preferably at least substantially each, package that is open on one side. How large the volume should actually be, is also ultimately related to the size and shape of the packages. Although the economical use of the preheating air, the drying air and/or the sterilising agent can generally be as preferred as a short treatment duration, for fluidic reasons, narrow and deep packages require higher media speeds and thus tend to require a higher volume overall for the desired treatment of the packages that are open on one side. On the other hand, in the case of narrow and deep packages, a larger proportion of the introduced volume actually comes into contact with the package, which in turn contributes to a tendency towards reduced media volumes. In contrast, in the case of flat and wide packages, a high speed is not required, only a small part of the introduced medium actually coming into contact or interacting with the package. An increase in the volume or the speed of the preheating air, the drying air and/or the sterilising agent can thus lead to increased turbulence and improved processing of the packages. Against this background, it can be expedient in certain applications if a volume of preheating air, drying air and/or sterilising agent, said volume corresponding to fifteen times, more particularly at least twenty times the volume of the package that is open on one side, is introduced into at least one, preferably at least substantially each, package that is open on one side.

The present method is particularly suitable when the at least one package that is open on one side is transported stepwise through the filling machine and is held in a plurality of successively arranged processing positions to be subjected to preheating air, drying air and/or sterilising agent. A plurality of successively arranged processing positions for subjecting the at least one package that is open on one side to preheating air can therefore be provided. Alternatively, or additionally, a plurality of successively arranged processing positions for subjecting the at least one package that is open on one side to drying air can be provided. In the same way, alternatively or additionally, a plurality of successively arranged processing positions for subjecting the at least one package that is open on one side to sterilising agent can be provided. Finally, the number of processing stations for filling one of said media is independent of the number of processing stations for filling another of said media. Simultaneous optimisation with regard to media consumption, the reliability of the processing of the packages and the duration of processing is then only possible to a limited extent. If the preheating, the drying and/or the sterilisation are carried out in a plurality of successively arranged processing positions, a certain quantity of media must be introduced into the package in each processing position. At the same time, the processing times must be divided and the reliability of the processing can additionally suffer from the processing being interrupted at least once in order to move the packages to be processed from one processing position to the next processing position. All these disadvantages can be taken into account by the surplus of preheating air, drying air and/or sterilising agent.

In connection with a plurality of processing positions for filling in one medium, either preheating air, drying air or sterilising agent it is particularly effective and efficient when a volume of preheating air, drying air and/or sterilising agent, said volume corresponding to at least three times, preferably at least four times, in particular at least six times, more preferably at least ten times, more particularly at least fifteen times, as necessary at least twenty times the volume of the package that is open on one side, is introduced into the at least one, preferably at least substantially each, package that is open on one side. In this way, reliable heating, drying and/or sterilisation is achieved with a low level of equipment and/or time expenditure. How large the volume of the medium used should actually be, is also ultimately related to the size and shape of the packages. Economical use of the preheating air, the drying air and/or the sterilising agent is as desirable as a short treatment duration. However, for fluidic reasons, narrow and deep packages require higher speeds of the medium and thus larger volumes of medium. On the other hand, in the case of narrow and deep packages, a larger proportion of the introduced volume actually comes into contact with the package, which in turn contributes to a tendency towards reduced media volumes. In contrast, in the case of flat and wide packages, a high speed is not required, only a small part of the introduced medium actually coming into contact or interacting with the package, which nevertheless necessitates a higher speed of the medium and/or a larger volume of the medium.

For example, in order to increase the application time of the preheating air, of the sterilising agent and/or of the drying air without requiring a greater volume, the packages that are open on one side can be held in at least two, preferably at least three, in particular at least four successively arranged processing positions for subjecting the packages to preheating air, drying air and/or sterilising agent. The packages that are open on one side can thus be held in at least two, preferably at least three, in particular at least four successively arranged processing positions and subjected to preheating air. Alternatively or additionally, however, the packages that are open on one side can also be held in at least two, preferably at least three, in particular at least four successively arranged processing positions and subjected to drying air. Also alternatively or additionally, the packages that are open on one side can be held in at least two, preferably at least three, in particular at least four successively arranged processing positions and subjected to sterilising agent.

In order to achieve reliable and rapid processing of the packages by the preheating air, the drying air and/or the sterilising agent, the packages that are open on one side can be subjected to a volumetric flow rate of preheating air, drying air and/or sterilising agent of at least 4 m$^3$/h, preferably at least 9 m$^3$/h, in particular at least 15 m$^3$/h, more particularly at least 20 m$^3$/h. The higher the volumetric flow rate, the more intensive the interaction of the corresponding medium with the package. In addition, more medium can interact with the package in a shorter time, which accelerates the overall processing. However, so that reliable and sufficient processing is achieved at the same time, a sufficient volume should likewise be introduced into the packages, which can be achieved by a volume that can exceed the package volume by a multiple.

The reliability and the processing time can also be positively influenced if the packages that are open on one side are subjected to preheating air at a temperature of between 80° C. and 340° C., preferably between 80° C. and 260° C., drying air at a temperature of between 80° C. and 340° C., preferably between 80° C. and 260° C. and/or sterilising agent at a temperature of between 170° C. and 340° C., preferably between 220° C. and 290° C., in particular between 260° C. and 280° C. In this way, satisfactory heat- and/or mass transfer is achieved. The temperatures are, as necessary, present in the filling machine before the exit of the corresponding medium from an outlet or after exit from the filling machine. In other words, the temperatures can be measured after exit if, for example, a corresponding temperature sensor is not provided in the filling machine.

The reliability of the processing of the packages with preheating air, drying air and/or sterilising agent can furthermore be increased if the preheating air, the drying air and/or the sterilising agent is introduced, in at least in one processing position, eccentrically with respect to the package via at least one corresponding nozzle as necessary into the packages. The packages can thus be heated, sterilised and/or dried uniformly without certain areas or edges of the interior of the packages that are open on one side making insufficient contact with the preheating air, the sterilising agent and/or the drying air. The atmosphere can then be displaced from the package in a more predictable manner than in a central and thus, to a certain extent, random or chaotic introduction of preheating air, drying air and/or sterilising agent into the packages. In the case of eccentric introduction of the media, a more targeted flow of the preheating air, of the sterilising agent and/or of the drying air and, in addition, a more targeted displacement of the atmosphere from the packages can ultimately be achieved. This leads to more uniform and more reliable treatment of the packages in a shorter time.

However, it is not absolutely necessary to introduce the preheating air, the sterilising agent and the drying air eccentrically. It may be sufficient to introduce only one medium or individual media eccentrically via a corresponding nozzle into the packages, and, as necessary, only in certain processing positions. In each individual case, this depends largely on the package geometry and the corresponding medium.

In the present case, the term "nozzle" is preferably understood to be very general. A nozzle with a significant cross-sectional narrowing is not necessarily required to generate a significant pressure loss or a greatly widening free jet. The nozzle is intended to enable a reliable and targeted delivery of the corresponding medium at a predetermined position, namely eccentrically, into the package. In a particularly simple case, the nozzle can be designed as a straight tube piece that can be aligned very precisely with the packages.

Particularly efficient and reliable processing of the packages can be achieved if, in order to introduce the preheating air, the drying air and/or the sterilising agent, the centre of the nozzle opening or even the entire nozzle opening is arranged laterally next to the central longitudinal axis, in particular the central vertical axis, of the package. In this way, a suitable eccentric arrangement of the at least one nozzle for introducing the preheating air, the drying air and/or of the sterilising agent is achieved. In this case, the centre of the nozzle opening or even the entire nozzle opening can, by at least the width of the corresponding nozzle opening, be arranged laterally next to the central longitudinal axis or vertical axis of the package that is open on one side. From the middle or the centre, the nozzle opening can be shifted to a side and/or to an edge of the nozzle opening of the package that is open on one side in order to achieve a suitable introduction of the corresponding medium. All this leads to reproducible and targeted processing of the packages.

Irrespective of the arrangement of the respective nozzle opening, the nozzle opening will be circular for the sake of simplicity. As necessary, however, a nozzle opening having an oval, rectangular, square or other design can also be considered for a faster exit of the corresponding medium from the nozzle opening and/or in order to optimise the flow in the package. Also irrespective of the shape of the nozzle opening, the ratio of the cross-sectional area of the nozzle opening to the cross-sectional area of the package opening can be between 10% and 50%, preferably between 15% and 40%, in particular between 20% and 30%. An expedient treatment of the package with preheating air, sterilising agent and/or drying air, and the filling of the product, are thus improved.

Alternatively or additionally, the at least one nozzle, in particular the nozzle opening thereof, is arranged offset with respect to the longitudinal axis of the package that is open on one side in a direction parallel and, alternatively or additionally, also perpendicular to the transport direction of the packages. The transport of the packages can thus be taken into account. This can be of particular importance because the packages are mostly transported in predetermined orientations in the transport direction. Thus, for example, a narrower side surface points in a direction approximately parallel to the transport direction and a wider side surface points in a direction approximately perpendicular thereto, in order to reduce sloshing of the product in the packages during cyclical, that is, stepwise transport of the package.

For the purpose of uniform and simple treatment of the packages, it is recommended for the preheating air, the sterilising agent and/or the drying air to be successively introduced from above via at least two nozzles, in particular in two consecutive processing positions in the filling machine, into the packages that are open on one side. In addition, for the sake of simplicity, use is made of cyclical transport of the packages. However, in order to increase the application time and reduce the use of corresponding medium, it can also be provided that, between two processing positions, at least one position exists in which the packages come to a standstill but are not processed. In this case, it can be particularly expedient if the at least two nozzles, during the introduction of the preheating air, the drying air and/or the sterilising agent into the package that is open on one side, are respectively positioned eccentrically with respect to the package that is open on one side. The advantages of the eccentric introduction are then utilised in two consecutive method steps. The nozzles can in this case be arranged eccentrically with respect to the packages at other locations for more uniform treatment of the packages.

Particularly good results can be achieved as necessary if the nozzles can be arranged, in at least two consecutive positions, approximately symmetrically, in particular point-symmetrically, in relation to the longitudinal axis of the package or to the vertical axis of the package. In other words, the at least two nozzles are arranged symmetrically, point-symmetrically or mirror-symmetrically in relation to the package that is open on one side. The mirror plane can, as necessary, also be provided parallel to the longitudinal axis of the package or to the vertical axis of the package, and, in addition, longitudinally, transversely, or so as to connect two diagonally opposite edges of the package.

When the packages that are open on one side are transported stepwise through the Ailing machine, the packages that are open on one side are, in each case, at times positioned in a stationary manner under at least one, preferably also stationary, nozzle. Said position can then be regarded as a processing position. During the corresponding period of time, preheating air, drying air and/or sterilising agent is then guided into the package by means of the corresponding nozzle.

The packages that are open on one side can be positioned under the at least one nozzle by a transport device that transports the packages. This enables simple and precise positioning of the packages relative to the at least one nozzle in order to introduce preheating air, drying air and/or sterilising agent into the packages. In this case, the processing of the packages, that is to say the heating, the sterilisation and/or the drying of the packages, is improved as necessary by the fact that the packages that are open on one side are positioned eccentrically relative to the at least one nozzle under the same.

The transport of the packages by the filling machine can be carried out very exactly and reliably if the transport device has a cell chain with cells for receiving packages that are open on one side. Alternatively or additionally, however, a belt drive with cells and/or a direct drive with, in particular separate, cells can also be provided. It is then also possible for the packages to be transported exactly and reliably. If the transport device is provided for stepwise transport of the packages that are open on one side through the filling machine, the packages can be positioned eccentrically in a very precise manner under the nozzles for introducing the preheating air, the drying air and/or the sterilising agent. This is achieved in a particularly reliable manner when the cell chain, in at least one processing position for positioning the packages that are open on one side, is designed eccentrically under the at least one nozzle for introducing preheating air, drying air and/or sterilising agent.

If, during the introduction of the preheating air, the drying air and/or the sterilising agent into the packages, the centre of the nozzle opening, preferably the entire nozzle opening, in particular by at least the width of a nozzle opening, is arranged laterally next to the central longitudinal axis of the packages that are open on one side, the advantages already described can be utilised to a particular extent through the eccentric introduction of preheating air, drying air and/or sterilising agent. In this case, the corresponding nozzle opening is then preferably assigned to one side and/or one edge of the package that is open on one side, in order to better utilise the corresponding advantages. Good results in the eccentric spacing of the nozzle are achieved as necessary when the nozzle or the midpoint of the nozzle is spaced from the central longitudinal axis by at least half the distance from the central longitudinal axis to one side and/or one edge of the corresponding package.

If, during the introduction of the preheating air, the drying air and/or the sterilising agent into the packages, the at least one nozzle, in particular the nozzle opening thereof, is arranged offset with respect to the longitudinal axis of the package that is open on one side in a direction parallel and/or perpendicular to the transport direction of the packages, the transport of the packages, in particular the package geometry and orientation of the packages that is regularly dependent on the transport direction, can be taken into account.

If at least two nozzles are provided for introducing preheating air, drying air and/or sterilising agent successively and from above into the packages that are open on one side, the corresponding introduction of medium can be divided into at least two method steps and can be carried out in a different manner in the at least two method steps. The at least two nozzles can, during the introduction of the preheating air, the drying air and/or the sterilising agent into the packages, be respectively positioned eccentrically relative to the package that is open on one side in order to increase the advantages to be achieved therewith. In this case, for the purpose of uniform treatment of the packages, it has proven particularly expedient for the at least two nozzles to be arranged symmetrically, point-symmetrically or mirror-symmetrically in relation to the packages that are open on one side.

For the sake of completeness, it should be noted that the preheating air, the drying air and/or the sterilising agent can be introduced in the same manner. However, it is also possible for only two of these media to be introduced in the same manner. Likewise, the preheating air, the drying air and the sterilising agent can also be introduced in different ways. This sameness or difference can relate to a centric or eccentric introduction of preheating air, drying air and/or sterilising agent as well as to the number of processing positions for introducing preheating air, drying air and/or sterilising agent. The introduction of said media can thus be adapted to the respective boundary conditions in order to be able to provide the most optimal method.

In addition, during the introduction of preheating air into at least two consecutive packages that are open on one side using at least one nozzle, the preheating air can flow out of the at least one nozzle at an at least substantially constant volumetric flow rate. Alternatively or additionally, during the introduction of drying air into at least two consecutive packages that are open on one side using at least one nozzle, the drying air can also flow out of the at least one nozzle at an at least substantially constant volumetric flow rate. Alternatively or additionally, during the introduction of sterilising agent into at least two consecutive packages that are open on one side using at least one nozzle, the sterilising agent can also flow out of the at least one nozzle at an at least substantially constant volumetric flow rate. In each of the cases mentioned, the corresponding medium then flows continuously out of at least one nozzle, for example, while consecutive packages are transported underneath. Between the processing of two consecutive packages, the outflow of the medium is thus not stopped. The medium also continues to flows out during package changes.

BRIEF DESCRIPTION OF THE DRAWINGS

The invention will be explained in more detail below on the basis of drawings illustrating only exemplary embodiments, wherein.

DESCRIPTION OF THE INVENTION

Figure 1:
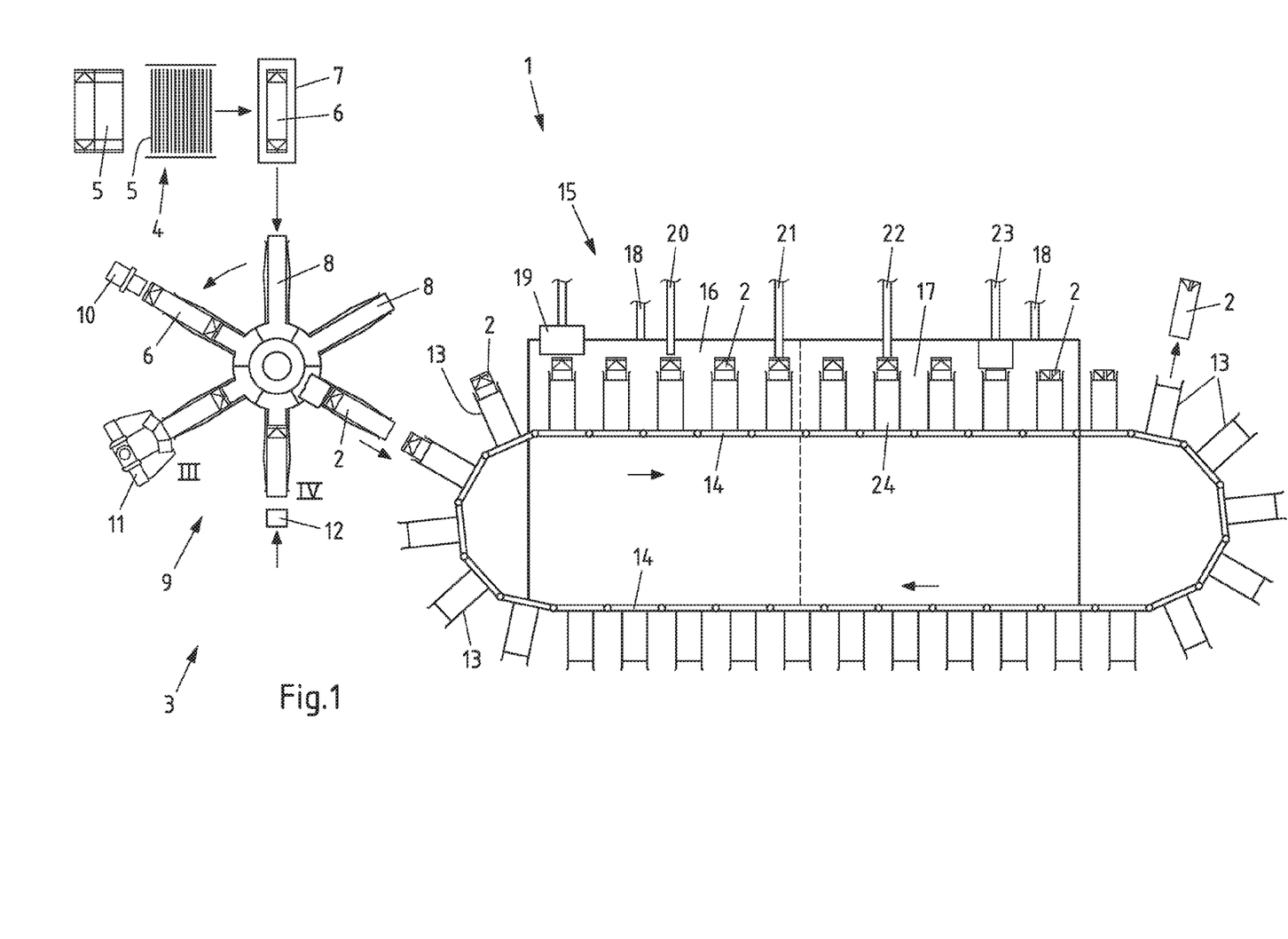
FIG. 1 shows a filling machine according to the invention for carrying out the method according to the invention in a schematic side view.

FIG. 1 depicts a filling machine 1 for filling packages 2, in particular with free-flowing foodstuffs, which in this case comprises a device 3 for forming the packages 2 to be filled. Generally, however, it is also possible for the filling machine to be fed the packages 2 that are open on one side and are already to be filled. The filling machine 1 depicted and in this respect preferred also has a series of parallel processing lines, of which only one processing line is depicted in FIG. 1. Each processing line is assigned a bundle 4 of package blanks 5, the longitudinal edges of which are sealed to one another and thus form package sleeves 6 that are open on both sides. The package sleeves 6 are unfolded by a feeding device 7 and pushed onto a mandrel 8 of a mandrel wheel 9.

The mandrel wheel 9 depicted and in this respect preferred is rotated anticlockwise in a cyclical, that is, stepwise, manner. The package sleeves 6 are processed in different positions. Firstly, an edge is heated with preheating air using a heating unit 10, and subsequently pre-folded in a pre-fold 11, in order to subsequently seal the pre-folded edge to a base using a press 12. A package 2 that is open on one side and tightly closed at one end is thus obtained, said package being transferred to a cell 13 of an endless transport device 14 that is guided in a circle. The filling machine 1 depicted and in this respect preferred is an endlessly circulating cell chain.

The package 2 is transported by the transport device 14 through an aseptic chamber 15, which is successively subdivided into a sterilisation zone 16 and a filling and sealing zone 17. The packages 2 do not have to be transported in a straight line, but can also be transported in at least an arc or even in a circle, depending on whether the filling machine 1 is a so-called inline machine or a rotary machine. The aseptic chamber 15 is flushed with sterile air via corresponding sterile air connections 18 in order to prevent the ingress of germs.

Sterile preheating air is firstly blown by a preheating device 19 into the packages 2 that are open at the top in order to preheat the packages 2. Subsequently, a sterilising agent is blown into the packages in a sterilising device 20, said sterilising agent reacting more strongly and condensing less in the preheated packages 2. Hydrogen peroxide in particular is suitable as a sterilising agent. The hydrogen peroxide can be introduced together with steam and/or air into the package 2 that is open on one side. After the sterilisation of the packages 2, the interior of the packages 2 is dried in a drying device 21 by being subjected to drying air. The drying air is preferably hot and sterile in this case.

After the transfer from the sterilisation zone 16 into the filling and sealing zone 17, the packages 2 that are open on one side are positioned under a filling device 22 and filled with a foodstuff. The filled packages 2 are then closed using a closing device 23, which folds the upper open region of the package 2 and seals said upper open region. The closed packages 2 are subsequently removed from the cells 13 of the transport device 14 and processed further as necessary. The now empty cells 13 of the transport device 14 are moved further in the direction of the mandrel wheel 9 in order to receive further packages 2 there.

Figure 2:
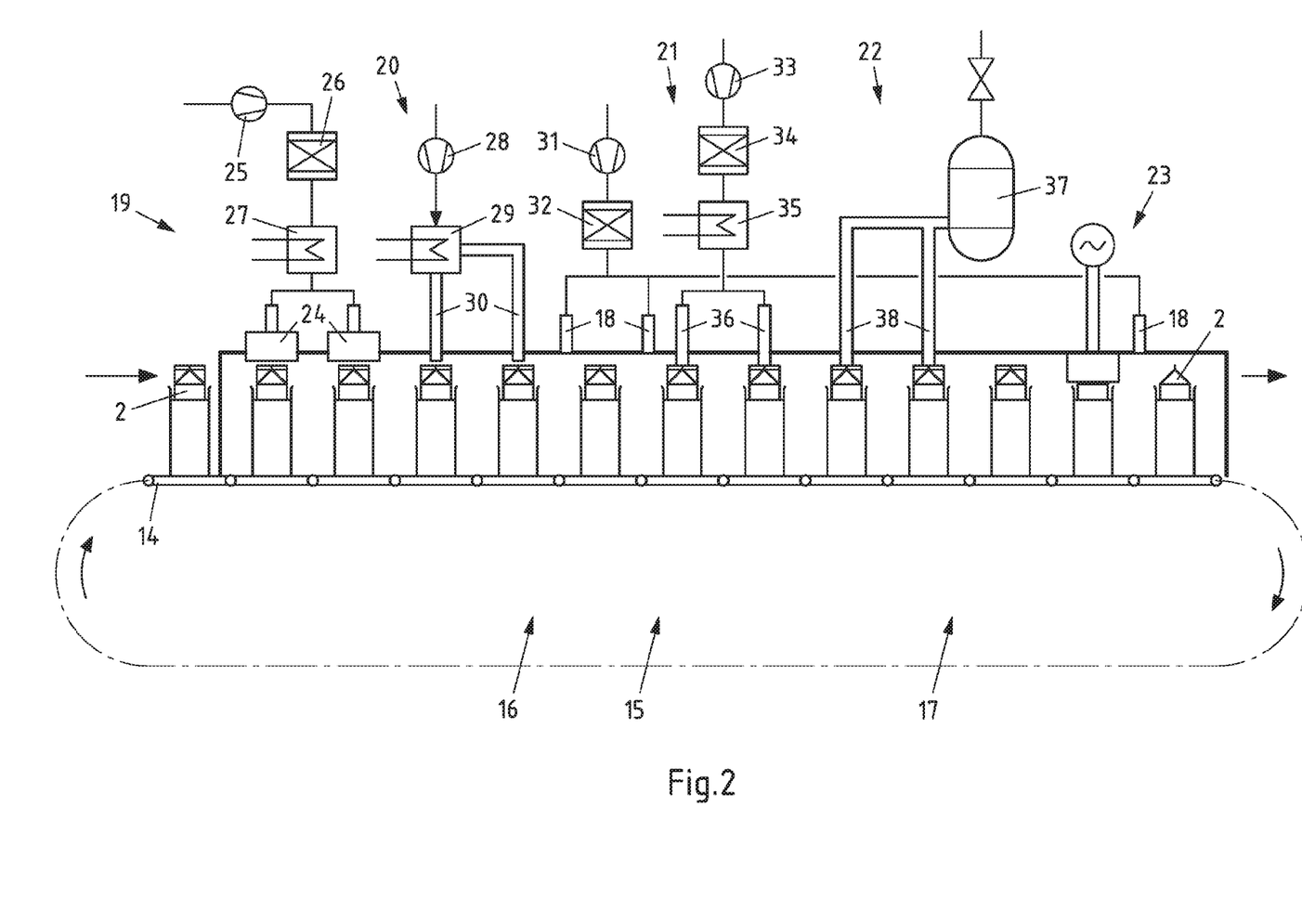
FIG. 2 shows a detail of the filling machine in a schematic side view.

In FIG. 1, the preheating device 19, sterilising device 20, drying device 21 and filling device 22 are only depicted schematically for the sake of greater clarity. The aseptic chamber 15 is therefore depicted again in detail in FIG. 2. The representation of FIG. 2 is also very schematic, although more positions are depicted in which the packages 2 are at times positioned during the stepwise transport through the aseptic chamber 15 by means of the transport device 14. Generally, it would also be possible to transport the packages 2 continuously without standstill and, as necessary, at a constant speed through the aseptic chamber 15. It would likewise be possible, for subjecting the packages 2 to preheating air, sterilising agent and/or drying air, to provide only a single processing position in which the packages 2 to be processed are held. Provision could also be made for a different number of processing positions to be provided for subjecting the packages 2 to preheating air than for subjecting the packages 2 to drying air and/or to sterilising agent, and vice versa.

In many cases, however, it will be preferred, at least for the heating, the sterilisation and/or the drying, to provide a plurality of processing positions in which the packages 2 to be processed are held to be subjected to the corresponding medium. As a result, however, the method is generally more complex and more difficult to control. In addition, corresponding filling machines 1 can also have different numbers of processing positions for the packages 2, preheating devices 19, sterilising devices 20, drying devices 21 and/or filling devices 22. The aseptic chamber 15 depicted and in this respect preferred, however, allows for a comprehensible description of the invention, so that representation of alternative aseptic chambers can be dispensed with.

In the aseptic chamber 15 of FIG. 2, a preheating device 19 is firstly provided in the sterilisation zone 16 that extends over two processing positions of the cell chain transport device 14. A nozzle 24 for introducing preheating air is provided in each of the two processing positions. In the case of the filling machine 1 depicted and in this respect preferred, the preheating air is sucked in from the environment via a compressor 25 and filtered with the aid of a filter 26 in order to separate microorganisms and thus sterilise the air. Subsequently, the sterile air is heated in a heating device 27. In each of the two processing positions, the packages 2 that are open on one side are positioned eccentrically under the stationary nozzles 24 of the preheating device 19, the central longitudinal axes of the packages 2 being offset in different ways in the two positions with respect to the corresponding nozzle 24. The preheating air is therefore introduced in different ways via the nozzles 24.

The volume of preheating air that is introduced into a package 2 is at least three times, four times, six times or even ten times the volume of the package, depending on the type of the package 2. This applies as necessary for subjecting the individual packages to preheating air together in the two processing positions. However, in each individual processing position for subjecting the packages to preheating air, a corresponding volume of preheating air can also be introduced into each individual package to be processed.

The next two positions of the sterilisation zone 16 serve to sterilise the packages 2 in a sterilising device 20 by means of a sterilising agent. In the filling machine 1 depicted and in this respect preferred, the sterilising agent is an aqueous hydrogen peroxide solution that is fed via a pump 28 and evaporated in an evaporator 29. The mixture of hydrogen peroxide and steam, which can still be fed with air, is introduced eccentrically via two nozzles 30 into the packages 2 positioned underneath. Each of the two nozzles 30 is spaced apart from the central longitudinal axis or the vertical axis of the packages 2 in a slightly different direction than the other nozzle 30 in each case.

The volume of sterilising agent that is introduced into a package 2 is at least three times, four times, six times or even ten times the volume of the package, depending on the type of the package 2. This applies as necessary in relation to subjecting the individual packages to sterilising agent together in the two processing positions. However, in each individual processing position for subjecting the packages to sterilising agent, a corresponding volume of sterilising agent can also be introduced into each individual package to be processed.

After the sterilisation, an empty position follows in which no processing of the packages 2 takes place in the filling machine 1 depicted and in this respect preferred. In this region, only sterile air is guided via sterile air connections 18 into the sterilisation zone 16. To this end, air is sucked in from the environment via a compressor 31 and compressed via a filter 32 in which all microorganisms are isolated in order to sterilise the air. In the following processing positions of the transport device 14 in the form of the cell chain, the packages 2 are dried in the drying device 21 with hot drying air, which is likewise sucked in via a compressor 33 and degermed in a filter 34. The air sterilised in this way is heated in a heating device 35 and guided eccentrically into the packages 2. In this case, each package 2 is arranged slightly differently under the nozzles 36. The nozzles 36 are positioned at other points above the cross section of the packages 2 during the introduction of the drying air, but in each case at a distance from the centre or the middle of the cross section.

The volume of drying air that is introduced into a package 2 is at least three times, four times, six times or even ten times the volume of the package, depending on the type of the package 2. This applies as necessary in relation to subjecting the individual packages to drying air together in the two processing positions. However, in each individual processing position for subjecting the packages to drying air, a corresponding volume of drying air can also be introduced into each individual package to be processed.

As necessary, the volumes of preheating air, drying air and sterilising agent per package are identical or also different. The volume of a medium can generally be selected so as to be different from the volumes of the other media.

The dried packages 2 are then transferred into the Ailing and sealing zone 17, where the packages 2 are filled with the product in the form of a foodstuff in the next two processing positions of the transport device 14. The product is fed in the Ailing device 22 via a storage container 37 and guided via two nozzles 38 into the packages. Each of the nozzles 38 is arranged eccentrically relative to the cross section of the packages 2, the nozzles 38 being positioned at other points in relation to the cross sections of the packages 2. The filled packages 2 are moved with the next cycle into a processing position in which the packages 2 are not processed further. In the following processing position, the package 2 is closed by a closing device 23, which seals the upper edge, and transported out of the aseptic chamber 15 after a further empty position.

Figure 3A:
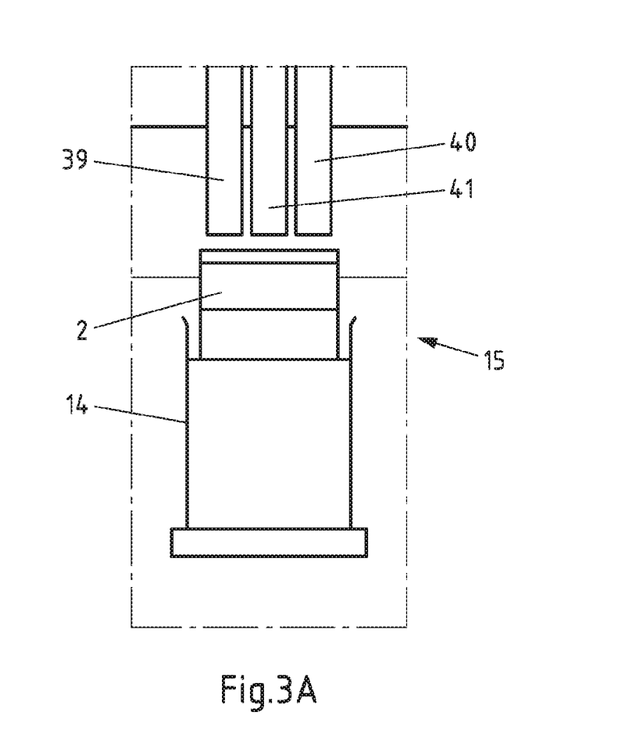
FIGS. 3A-B show the introduction of preheating air, drying air, sterilising agent and/or product to be filled in a schematic side view and a schematic plan view
Figure 3B:
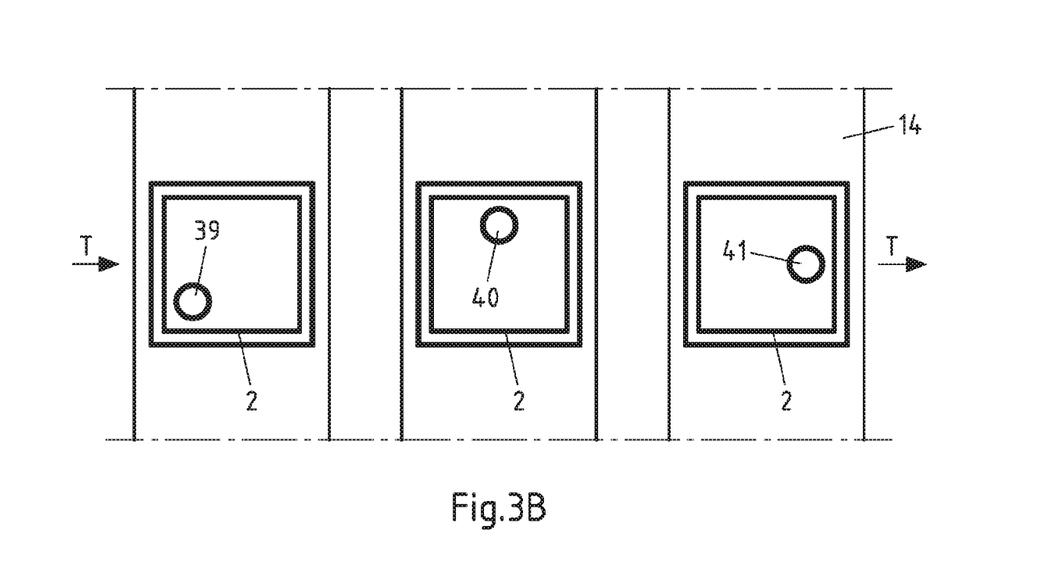

FIGS. 3A-B depict the introduction of preheating air, drying air, sterilising agent and/or product to be filled in a side view counter to the transport direction T and in a plan view from above in which the transport direction of the packages 2 is indicated by arrows. The package 2 is held in a cell of a transport device 14 and, during the introduction of preheating air, drying air, sterilising agent or product to be filled, is transported further, stepwise, over three processing positions and positioned in each processing position in a stationary manner under a stationary nozzle 39, 40, 41 for a certain time. Each nozzle 39,40, 41 is arranged eccentrically relative to the cross section of the package 2 positioned underneath. In the first processing position, the nozzle 39 is spaced counter to the transport direction T and to the right side, in relation to the transport direction T, of the middle of the package 2, which is defined by the middle of the cross section or the central longitudinal axis of the package 2. In other words, the nozzle 39 is arranged at the back right in the region of the edge of the package 2. In the second processing position, the nozzle 40 is spaced, viewed in the transport direction T, to the left of the middle of the cross section of the package 2 positioned underneath. In the third processing position, the nozzle 41 is spaced in the transport direction T counter to the middle of the cross section of the package 2. However, this constitutes only one possible embodiment.

Figure 4:
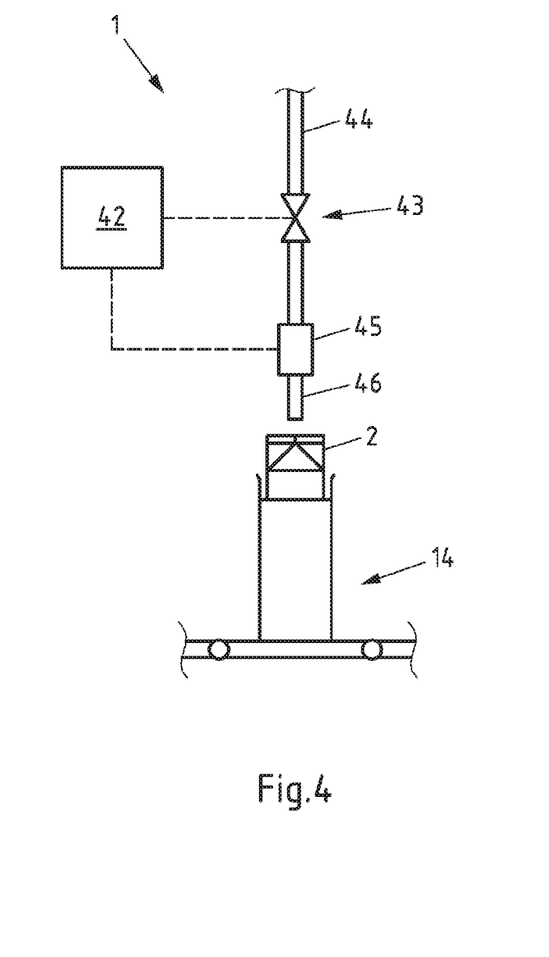
FIG. 4 shows an arrangement of adjustment means and introduction means for introducing a volume of preheating air, drying air and/or sterilising agent into the packages that are open on one side in a schematic representation.

FIG. 4 schematically depicts an arrangement of adjustment means 42 and introduction means 43 of a filling machine 1 for introducing a volume of preheating air, drying air and/or sterilising agent into the packages 2 that are open on one side. Since the adjustment means 42 and introduction means 43 can generally be designed and arranged quite differently, the schematic representation according to FIG. 4 is sufficient. The person skilled in the art will be capable, on the basis of the present description and on the basis of his/her expert knowledge, to design the filling machine 1 in a suitable manner and to this end use, for example, devices known from the prior art. A line 44 for preheating air, drying air and/or sterilising agent is depicted in FIG. 4. The corresponding medium is under an overpressure in the line and is released via the introduction means 43 in the form of a shut-off element in particular a valve. The shut-off element can be opened and closed by an adjustment means 42, in particular in the form of a regulating device and/or control device. The medium passing through the introduction means 43 travels through a flow sensor 45, which determines the volume and/or the mass of the medium passing through the introduction means 43, before the medium is introduced via a nozzle 46 into a package 2 that is open on one side and positioned under the nozzle 46. The quantity of medium detected by the flow sensor 45 is transmitted to the adjustment means 42 for the purpose of regulation and/or for the purpose of documentation.

LIST OF REFERENCE SIGNS

1 Filling machine
2 Package
3 Device
4 Bundle
5 Blank packages
6 Package sleeves
7 Feeding device
8 Mandrel
9 Mandrel wheel
10 Heating device
11 Pre-folds
12 Press
13 Cells
14 Transport device
15 Aseptic chamber
16 Sterilisation zone
17 Filling and sealing zone
18 Sterile air connection
19 Preheating device
20 Sterilising device
21 Drying device
22 Filling device
23 Closing device
24 Nozzle
25 Compressor
26 Filter
27 Heating device
28 Pump
29 Evaporator
30 Nozzle
31 Compressor
32 Filter
33 Compressor
34 Filter
35 Heating device
36 Nozzle
37 Storage container
38-41 Nozzle
42 Adjustment means
43 Introduction means
44 Line
45 Flow sensor
46 Nozzle

The invention claimed is:

1. A method for filling packages that are open on one side with free-flowing products in a filling machine, wherein the packages are cardboard composite packages consisting of a laminate comprising a cardboard layer and outer thermoplastic layers made of polyethylene, the method comprising:
introducing at least one of preheating air, drying air, or sterilizing agent successively from above via at least two nozzles into at least one of the packages that are open on one side;
respectively positioning each of the at least two nozzles in one of a plurality of successively arranged processing positions during the introduction of the at least one of preheating air, drying air, or sterilizing agent into the at least one of the packages that are open on one side, wherein each nozzle is eccentrically located at a different position relative to a central longitudinal axis of the at least one of the packages that are open on one side;

arranging the at least two nozzles mirror-symmetrically in relation to the at least one of the packages that are open on one side;

transporting the at least one of the packages that are open on one side stepwise through the filling machine and holding the at least one of the packages that are open on one side in the plurality of successively arranged processing positions to be subjected to the at least one of preheating air, drying air, or sterilizing agent; and introducing a volume of the at least one of preheating air, drying air, or sterilizing agent into the at least one of the packages that are open on one side, wherein said volume corresponds to at least three times the volume of each of the packages that are open on one side.

2. The method according to claim 1, wherein said volume corresponds to at least four times the volume of each of the packages that are open on one side.

3. The method according to claim 1, further comprising: introducing said volume of the at least one of preheating air, drying air, or sterilizing agent into the at least one of the packages that are open on one side in at least one processing station.

4. The method according to claim 3, further comprising: holding the at least one of the packages that are open on one side in at least two of the successively arranged processing positions to be subjected to the at least one of preheating air, drying air, or sterilizing agent.

5. The method according to claim 1, further comprising: subjecting the at least one of the packages that are open on one side to a volumetric flow rate of the at least one of preheating air, drying air, or sterilizing agent of at least 4 m$^3$/h.

6. The method according to claim 1, further comprising: subjecting the at least one of the packages that are open on one side to preheating air at a temperature of between 80° C. and 340° C., drying air at a temperature of between 80° C. and 340° C., and/or sterilizing agent at a temperature of between 170° C. and 340° C.

7. The method according to claim 1, further comprising: arranging a center of a nozzle opening of one of the at least two nozzles laterally next to the central longitudinal axis of the at least one of the packages that are open on one side during the introduction of the at least one of preheating air, drying air, or sterilizing agent into at least one of the packages that are open on one side.

8. The method according to claim 1, further comprising: arranging one of the at least two nozzles offset relative to the central longitudinal axis of the at least one of the packages that are open on one side in a direction parallel and/or perpendicular to a transport direction of the packages.

9. The method according to claim 1, further comprising: positioning the at least one of the packages that are open on one side at times in a stationary manner under one of the at least two nozzles.

10. The method according to claim 1, further comprising: introducing the at least one of preheating air, drying air, or sterilizing agent into at least two consecutive packages that are open on one side using one of the at least two nozzles, wherein the at least one of preheating air, drying air, or sterilizing agent flows out of the one of the at least two nozzles at a constant volumetric flow rate.

11. The method according to claim 7, further comprising: assigning the nozzle opening of the one of the at least two nozzles to one side and/or one edge of the at least one of the packages that are open on one side.

12. A filling machine for filling packages that are open on one side with free-flowing products, wherein the packages are cardboard composite packages consisting of a laminate comprising a cardboard layer and outer thermoplastic layers made of polyethylene, the filling machine comprising:

at least two nozzles configured to successively introduce at least one of preheating air, drying air, or sterilizing agent from above into at least one of the packages that are open on one side;

a transport device configured to transport the at least one of the packages that are open on one side stepwise through the filling machine and to hold the at least one of the packages that are open on one side in a plurality of successively arranged processing positions for subjecting the at least one of the packages that are open on one side to the at least one of preheating air, drying air, or sterilizing agent, wherein each of the at least two nozzles is respectively positioned in one of the plurality of successively arranged processing positions during the introduction of the at least one of preheating air, drying air, or sterilizing agent into the at least one of the packages that are open on one side, wherein each nozzle is eccentrically located at a different position relative to a central longitudinal axis of the at least one of the packages that are open on one side, and wherein the at least two nozzles are arranged mirror-symmetrically in relation to the at least one of the packages that are open on one side; and an adjuster and an introducer configured to introduce a volume of the at least one of preheating air, drying air, or sterilizing agent into the at least one of the packages that are open on one side, wherein said volume corresponds to at least three times the volume of each of the packages that are open on one side.

13. The filling machine according to claim 12, wherein said volume corresponds to at least four times the volume of each of the packages that are open on one side.

14. The filling machine according to claim 12, wherein the transport device is configured to position the at least one of the packages that are open on one side eccentrically relative to one of the at least two nozzles during introduction of the at least one of preheating air, drying air, or sterilizing agent into the at least one of the packages.

15. The filling machine according to claim 14, wherein the transport device comprises at least one of a cell chain with cells, a belt drive with cells, or a direct drive with cells configured to receive the packages that are open on one side.

16. The filling machine according to claim 15, wherein the cell chain is configured to position the packages that are open on one side, in at least one step, eccentrically under one of the at least two nozzles.

* * * * *